United States Patent
Kwon et al.

(10) Patent No.: US 8,940,922 B2
(45) Date of Patent: Jan. 27, 2015

(54) ESTER-BASED REACTIVE PLASTICIZER FOR PLASTIC BONDED EXPLOSIVES

(71) Applicant: Agency For Defense Development, Daejeon (KR)

(72) Inventors: Young Hwan Kwon, Daegu (KR); Jin Seuk Kim, Daejeon (KR); Bum Jae Lee, Daejeon (KR); In Joo Bae, Daejeon (KR)

(73) Assignee: Agency For Defense Development, Daejeon (KR)

( * ) Notice: Subject to any disclaimer, the term of this patent is extended or adjusted under 35 U.S.C. 154(b) by 0 days.

(21) Appl. No.: 13/949,779

(22) Filed: Jul. 24, 2013

(65) Prior Publication Data

US 2014/0031580 A1    Jan. 30, 2014

(30) Foreign Application Priority Data

Jul. 25, 2012 (KR) .................. 10-2012-0081305

(51) Int. Cl.
    *C07C 205/51*    (2006.01)
(52) U.S. Cl.
    CPC .................... *C07C 205/51* (2013.01)
    USPC ........................................ 560/156

(58) Field of Classification Search
    CPC ............................ C07C 201/12; C06B 25/00
    See application file for complete search history.

(56) References Cited

U.S. PATENT DOCUMENTS

| | | |
|---|---|---|
| 3,655,836 A | 4/1972 | Dehm et al. |
| 4,108,926 A | 8/1978 | Arnold et al. |
| 5,061,330 A | 10/1991 | Reed, Jr. et al. |
| 5,520,756 A | 5/1996 | Zeigler |
| 6,736,913 B1 | 5/2004 | Hatch |

OTHER PUBLICATIONS

Nikolaeva et al, Zhurnal Organicheskoi Khimii, Reaction of Dinitrogen Tetroxide with Acyl Derivatives of Alkynediols, (1975), 11(4), pp. 691-695, English Abstract.*
WYPYCH, George, Handbook of Plasticizers, 2004, pp. 20-23, 66-67.
Advance in Research of Energetic Plasticizers, Chemical Propellants & Polymeric Materials, 5(1), 2003, 9 pages.

* cited by examiner

*Primary Examiner* — Paul A Zucker
(74) *Attorney, Agent, or Firm* — Harness, Dickey & Pierce, P.L.C.

(57) ABSTRACT

Disclosed is an energetic reactive plasticizer for a plastic bonded explosive (PBX), and specifically an energetic reactive plasticizer for PBX which has high performance and insensitiveness without a plasticizer migration by being bonded with a polymer binder for a plastic bonded explosive.

3 Claims, 2 Drawing Sheets

ESTER-BASED REACTIVE PLASTICIZER FOR PLASTIC BONDED EXPLOSIVES

CROSS-REFERENCE TO RELATED APPLICATION

This application claims the benefit and priority of Korean Patent Application No. 10-2012-0081305 filed Jul. 25, 2012. The entire disclosure of the above application is incorporated herein by reference.

TECHNICAL FIELD

The present invention relates to an energetic reactive plasticizer for a plastic bonded explosive, and specifically to an energetic reactive plasticizer for a plastic bonded explosive which has high performance and insensitiveness without a migration problem of a plasticizer by being bonded with a polymer binder for a plastic bonded explosive.

BACKGROUND ART

Currently, efforts to make energetic materials insensitive have been a significant issue in development of explosives and a propellant. As a part of such efforts, plastic bonded explosives (PBXs) having low sensitivity and improved mechanical properties while maintaining high energy properties have been developed. Such PBX now becomes an elementary component of high-energy explosives, polymeric binders and other additives used in a small amount such as a plasticizer or a stabilizer.

Currently, a polyurethane polymeric binder on the basis of a hydroxyl-terminated polybutadiene (HTPB) has been used as a widely applicable polymeric binder system, together with various additives so as to improve processability, mechanical properties and chemical stability. Although such polymeric binder shows excellent properties in making high-energy materials insensitive, it has been proposed that it generally disadvantageously reduces the energy density of PBX on the whole owing to its low energy potential. In this regard, many studies have been being made to increase the whole energy density through development of energetic binders and plasticizers containing energetic functional groups such as, for example, nitro ($C-NO_2$), nitrate ($O-NO_2$), nitramine ($N-NO_2$), azido ($-N_3$) and difluoroamino ($-NF_2$) and application thereof.

The term "energetic functional groups" as used herein has common and general meaning as used in the field of molecular explosives, i.e., referring to functional groups, when being applied to a molecular explosive or a plasticizer, known to contribute to the increase in the whole energy level of PBX to which the explosive or plasticizer were applied. Nitro ($C-NO_2$), nitrate ($O-NO_2$), nitramine ($N-NO_2$), azido ($-N_3$), difluoroamino ($-NF_2$) or the like as described above may be mentioned. The term "energetic" as used herein means that the whole energy level of a molecular explosive is more increased by any known methods comprising the introduction of such "energetic" functional groups.

However, those polymeric binders and plasticizers which comprise such energetic functional groups have problems such as low heat stability, non-compatibility with explosives and low processability. Therefore, it has been an important rising issue to ultimately achieve both high performance and insensitiveness in explosives. Further, when an energetic plasticizer is applied, an additional problem such as a migration of the energetic plasticizer from PBX occurs over a long period of time. Such migration of an energetic plasticizer involves further additional problems in PBX such as increase in sensitivity to impact and decrease in storage stability and long-term stability owing to deterioration in mechanical properties. Therefore, the realization of an explosive having both high performance and insensitiveness still has been an important matter to be achieved in this field of art.

When a highly energetic polymer which can satisfy both high performance and insensitiveness at the same time is prepared, it is anticipated to obtain a novel energy material which is combined with a molecular explosive and a binder and has an excellent performance and safety.

SUMMARY OF THE INVENTION

The present invention is to provide an energetic reactive plasticizer which can satisfy the high performance and insensitiveness required in the next-generation explosives without a plasticizer migration and thereby preventing various problems accompanied with such migration.

DETAILED DESCRIPTION OF THE INVENTION

PBX is majorly composed of a molecular explosive and a prepolymer and a curing agent for the formation of a binder, and additionally comprises other additives such as a plasticizer on necessary. All the components are introduced, mixed together and then loaded into a container for an explosive, this procedure of which is called a casting process. The prepolymer and the curing agent react in the container to form a binder while solidifying the components in the container.

The 'reactive plasticizer' is a high energy alkyne compound having low viscosity, which can be served as a plasticizer during mixing of PBX and attached to a polymer in a casting or curing process as above. The reactive plasticizer acts as a plasticizer in the preparation of PBX, and a part of or the whole plasticizer is bound into a binder by click reaction by itself in a curing process of the final preparation process.

The present inventors have found that by using a reactive plasticizer in a way of introducing high energy prepolymers in PBX preparation process, it acts as a plasticizer during the casting process, thereby solving the conventional viscosity problem and further it binds to a binder during a curing process, thereby reducing bleeding or migration of a plasticizer, and thus completed the present invention.

In other words, the present invention provides a novel reactive plasticizer having high energy potential by comprising a high energy functional group as well as a functional group which can react with a corresponding energetic prepolymer/a curing agent during a curing process in the preparation of a binder for PBX, thereby being bound to the high energy polymer binder as a side chain thereof.

The energetic reactive plasticizer according to the present invention binds with a side chain of a binder via a click reaction between azide and acetylene groups during the curing process. For such reaction, the energetic reactive plasticizer of the present invention comprises acetylene functional groups and the bond between the energetic functional group and the reactive functional group is an ester bond. In this regard, the novel energetic reactive plasticizer according to the present invention may be classified as an ester-based reactive plasticizer having high energy potential, considering the type of bond characteristically formed in the backbone of the compound is an ester bond.

The ester-based energetic reactive plasticizer is an ester-based compound obtained according to the following reaction scheme 1:

[Reaction scheme 1]

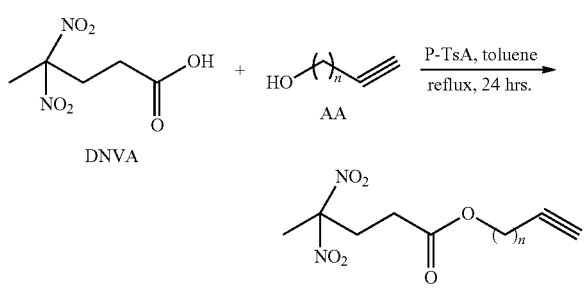

(wherein, n=a natural number selected from 1-10).

As seen from the above reaction scheme 1, the reactive energetic plasticizer containing ester groups in the backbone chain is formed by the acetal formation reaction between 4,4-dinitrovaleric acid (DNVA) and an acetylene-containing alcohol (AA).

The acetal formation reaction may be carried out under the conventional reaction conditions known in this field of art and thus an energetic reactive plasticizer comprising ester groups in the backbone chain is synthesized.

The acetylene-containing alcohol used in the above reaction includes for example, propargyl alcohol (n=1) and 3-butyn-1-ol (n=2), resulting in prop-2-yn-1-yl-4,4-dinitropentanoate (PDNP) or but-3-yn-1-yl-4,4-dinitropentanoate (BDNP), respectively.

EXAMPLES

Preparation Example 1

Synthesis and Analysis of prop-2-yn-1-yl-4,4-dinitropentanoate (PDNP)

An energetic reactive plasticizer, prop-2-yn-1-yl-4,4-dinitropentanoate was synthesized as shown in the following reaction scheme 2.

[Reaction scheme 2]

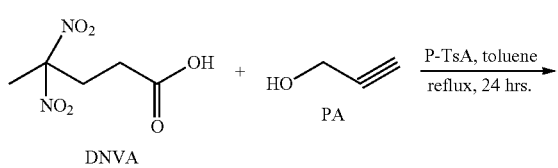

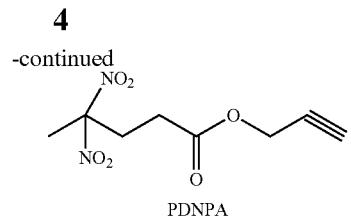

50 mL toluene, 4,4-dinitrovaleric acid (DNVA) (6.45 g, 33.56 mmol) and propargyl alcohol (PA) (5.64 g, 100.68 mmol) were placed into a 2-neck flask under nitrogen atmosphere, and then the mixture was refluxed for 24 hours. Water generated during reflux was continuously removed. After completing the reaction, the reactants were cooled, neutralized with 2N sodium hydroxide solution and extracted with ether. Thus extracted organic solution was washed with water and dried by using $MgSO_4$; the solvent was removed under reduced pressure; and the resultant was purified by column chromatography. The conformation of thus obtained energetic reactive plasticizer PDNP was identified by the following methods. $^1H$ and $^{13}C$ NMR were used to identify the molecular structure, resulting in: $^1H$ NMR ($CDCl_3$, d, ppm): 2.11 (3H, —$CH_3$), 2.49 (1H, =C—H), 2.50 (2H, —$CH_2$—COO—), 2.83 (2H, —$CH_2$—$CH_2$—), 4.677 (—O—$CH_2$—). $^{13}C$ NMR ($CDCl_3$, d, ppm): 22.4, 28.4, 31.6, 53.0, 75.8, 77.2, 118.8, 170.0.

Preparation Example 2

Synthesis and Analysis of but-3-yn-1-yl-4,4-dinitropentanoate (BDNP)

An energetic reactive plasticizer, but-3-yn-1-yl-4,4-dinitropentanoate was synthesized as shown in the following reaction scheme 3.

[Reaction scheme 3]

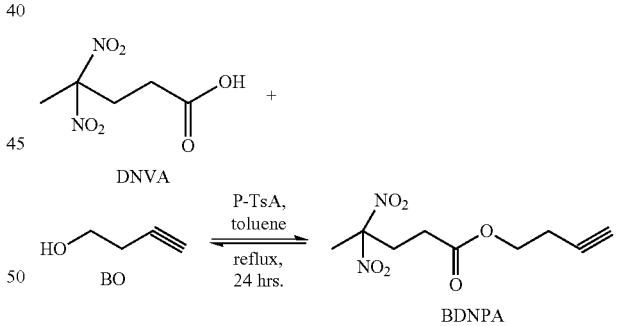

50 mL toluene, 4,4-dinitrovaleric acid (DNVA) (6.45 g, 33.56 mmol) and 3-butyn-1-ol (BO) (100.68 mmol) were placed into a 2-neck flask under nitrogen atmosphere, and then the mixture was refluxed for 24 hours. Water generated during reflux was continuously removed. After completing the reaction, the reactants were cooled, neutralized with 2N sodium hydroxide solution and extracted with ether. Thus extracted organic solution was washed with water and dried by using $MgSO_4$; the solvent was removed under reduced pressure; and the resultant was purified by column chromatography. The conformation of thus obtained energetic reactive plasticizer was identified by the following methods. $^1H$ and $^{13}C$ NMR were used to identify the molecular structure, resulting in: $^1H$ NMR ($CDCl_3$, d, ppm): 1.99 (1H, =C—H), 2.10 (3H, —CH₃), 2.46 (2H, —CH₂—CH₂—), 2.49 (2H, —CH₂—COO—), 2.82 (2H, —CH₂—CH₂—), 4.16 (2H, —O—CH₂—). ¹³C NMR (CDCl₃, d, ppm): 18.9, 22.4, 28.6, 31.6, 63.1, 70.6, 80.1, 119.0, 170.5.

Thus obtained plasticizer for the preparation of PBX and a prepolymer were mixed together in order to estimate the plasticization properties by measuring decrease in viscosity and glass transition temperature of said mixture, and the results were represented by the following test examples.

Test Example 1

Decrease in Viscosity of a Prepolymer Due to the Plasticizer

Figure 1:
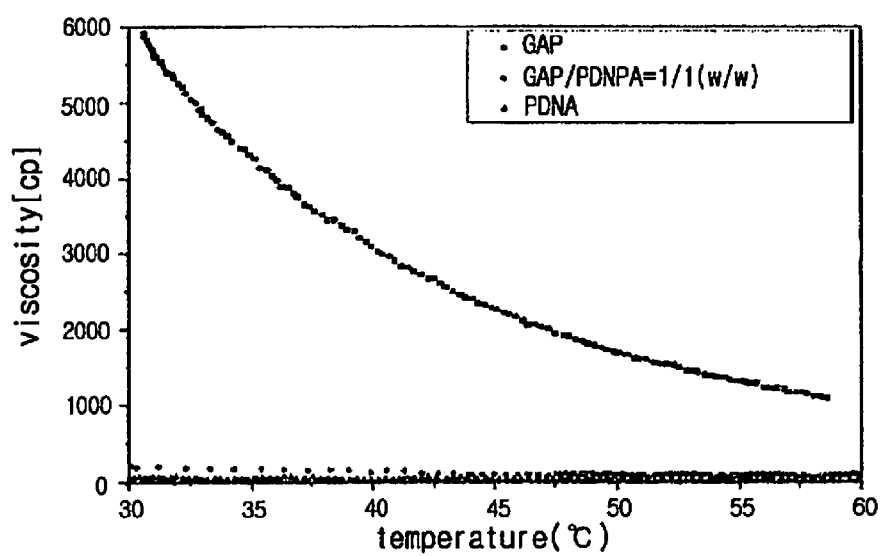
FIG. 1 is a plot showing viscosity changes of GAP polyol prepolymer, prepared PDNP and a mixture thereof (1:1 by weight) over temperature, respectively, as measured in the test example 1.

For measuring viscosity, a viscometer, MCR 301 from Anton Paar Physica Co. was used by using a parallel plate having a 1 mm gap (CP25-1-SN9356, diameter=25 mm) at the temperature range of 30-60° C. at a constant shear rate of 1.0 s⁻¹ with a temperature elevation rate of 1° C./minutes. After measuring viscosity of GAP polyol prepolymer per se, viscosity of a mixture of the plasticizer obtained by the above preparation example 1 or 2 and the GAP polyol prepolymer (1:1 w/w) was measured, so as to determine the plasticization properties represented by the decrease in viscosity. The test results obtained from the case wherein a plasticizer obtained according to the preparation example 1, i.e. PDNP was applied were represented in FIG. 1. As shown in FIG. 1, as compared to viscosity of a GAP polyol prepolymer, viscosity of a mixture of the plasticizer prepared according to the present invention and a GAP polyol prepolymer was significantly lowered, over the whole temperature range measured, thereby showing the significant plasticizing effect of the synthesized plasticizer according to the present invention.

The plasticizing effect represented by the decrease in viscosity of a conventionally used energetic plasticizer such as BDNPF/BDNPA; BDNPF/BDNPDF; BDNPF/BDNBF was also shown in the following table 1 for comparison. Viscosity was measured under the same test conditions as described in relation with viscosity measurement of the plasticizer prepared according to the present invention. For reference, viscosity of GAP polyol prepolymer itself was 6,015 cP at 30° C. and 1,035.5 cP at 60° C., respectively.

TABLE 1

Viscosity of a mixture of GAP polyol prepolymer/plasticizer(1:1 w/w) at 30° C. and 60° C.

| Composition (1:1 w/w) | Viscosity(cP) | |
|---|---|---|
| | 30° C. | 60° C. |
| GAP:PDNP | 224 | 76 |
| GAP:BDNP | 239 | 46 |
| GAP:BDNPF/BDNPA | 1,441 | 295 |
| GAP:BDNPF/BDNPDF | 1,211 | 197 |
| GAP:BDNPF/BDNBF | 1,351 | 274 |

BDNPF: bis(2,2-dinitropropyl) formal
BDNPA: bis(2,2-dinitropropyl) acetal
BDNPDF: bis(2,2-dinitropropyl) diformal
BDNBF: bis(2,2-dinitrobutyl) formal As seen from Table 1, it can be confirmed that the PDNP and BDNP plasticizer prepared according to the present invention have an excellent viscosity lowering effect in the GAP polyol prepolymer.

Test Example 2

Figure 2:
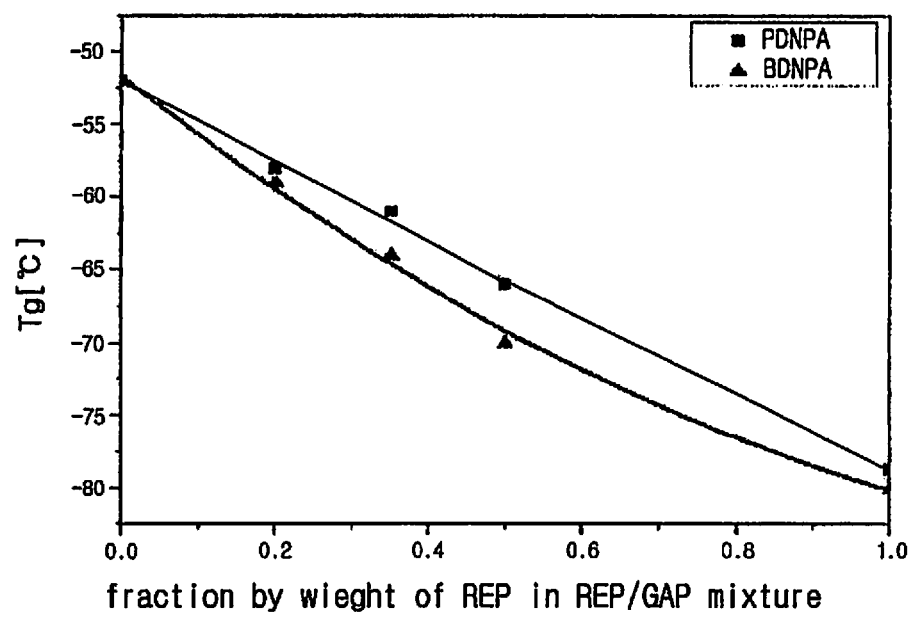
FIG. 2 is a plot showing changes in glass transition temperature of GAP polyol prepolymer depending on the content of the prepared plasticizer measured as in the test example 2.

Compatibility of the Plasticizer with a Prepolymer Measured by Glass Transition Temperature In FIG. 2, the changes in glass transition temperature of GAP polyol prepolymer depending on the increase of the weight fraction of the above-prepared reactive plasticizer (REP) were represented. PDNP and BDNP synthesized according to the above preparation examples 1 and 2, respectively were used and the weight fraction thereof was 0.2, 0.35 and 0.5, respectively. One glass transition temperature was measured in every composition of the tested plasticizer/prepolymer mixture, and it was confirmed that the obtained glass transition temperature met the Fox equation. This shows that the plasticizer prepared according to the present invention is compatible with GAP polyol prepolymer and has plasticizing effect on GAP polyol prepolymer.

INDUSTRIAL APPLICABILITY

The energetic reactive plasticizer according to the present invention is designed to be present in a form bound to the polymeric binder through covalent bond with the branch of the polymeric backbone of polymeric binder during a curing process, so as to prevent a conventional migration or exudation problem of an energetic plasticizer from the molded plastic PBX, while ensuring the essential physical properties required in an energetic plasticizer used in plastic PBX preparation, such as increased energy density and enhanced processability by lowered viscosity in a blending process.

When the energetic reactive plasticizer according to the present invention is applied to the plastic PBX preparation, the conventional plasticizer migration problem from plastic PBX can be prevented, leading to further advantageous effects such as an improvement in long term storage property of PBX and energy density increase in the whole composition.

What is claimed is:

1. An ester compound represented by the following chemical formula:

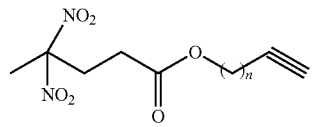

wherein n is a natural number of 1-10.

2. A method for preparing an ester compound according to claim 1, comprising:
    carrying out an esterification reaction between 4,4-dinitrovaleric acid and an alcohol containing an acetylene group.

3. A method for preparing a plastic bonded explosive, comprising:
    adding, to a reaction to prepare the plastic bonded explosive, an ester compound represented by the following chemical formula:

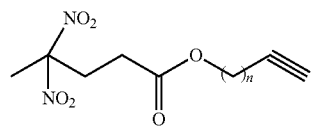
wherein n is a natural number of 1-10.
* * * * *